United States Patent [19]

Gadow

[11] Patent Number: 4,871,660
[45] Date of Patent: Oct. 3, 1989

[54] LUMINESCENCE IMMUNO-TEST KITS, METHOD FOR STABILIZING SAME AND QUALITY CONTROL THEREOF

[75] Inventor: Andre Gadow, Berlin, Fed. Rep. of Germany

[73] Assignee: Henning Berlin GmbH, Berlin, Fed. Rep. of Germany

[21] Appl. No.: 24,470

[22] Filed: Mar. 11, 1987

[30] Foreign Application Priority Data

Mar. 14, 1986 [DE] Fed. Rep. of Germany ....... 3608546

[51] Int. Cl.$^4$ .......................... G01N 33/00; C12Q 1/30
[52] U.S. Cl. ............................................ 435/7; 435/8; 435/27; 435/192; 435/810; 436/528; 436/63; 436/808
[58] Field of Search ...................... 422/292; 435/7, 27, 435/8, 192, 291, 810; 436/528, 63, 808

[56] References Cited

U.S. PATENT DOCUMENTS 2,689,203 9/1954 Lolli ................................. 435/192 X
4,104,029 8/1978 Maier, Jr. ................................. 435/7

OTHER PUBLICATIONS

White, C. E. et al., *Fluorescence Analysis, A Practical Approach*, Marcel Dekker, New York, pp. 256–259 (1970).

Primary Examiner—Esther M. Kepplinger
Assistant Examiner—Richard Wagner
Attorney, Agent, or Firm—Wegner & Bretschneider

[57] ABSTRACT

Luminescence immuno-test kits consist of an antigen or antibody capable of showing luminescence and labelled with phthalic hydrazides, an antibody or antigen preferably bound to a carrier and an oxidizing reagent inducing the luminescence to occur and are characterized in that the oxidizing reagent is a pre-fabricated solution of catalase, optionally stabilized by a bacteriostat, and the initiator is a pre-fabricated peroxide solution which is at least 20 minutes old. These luminescence immuno-tests are particularly stable and may be subjected to a quality control in a simple and inexpensive way.

14 Claims, 4 Drawing Sheets

FIG. 2

STABILITY OF VARIOUS READY-TO-USE CATALASE SOLUTIONS

| | TEMP. | FRESH | 6 DAYS | 12 DAYS | 25 DAYS | 35 DAYS | 2 MONTHS | 3 MONTHS | 4 MONTHS | 6 MONTHS |
|---|---|---|---|---|---|---|---|---|---|---|
| CATALASE SOLN. WITHOUT SODIUM AZIDE | 4°C | 100 | 97 | 92 | 104 | 102 | 110 | 108 | 102 | 101 |
| | RT | 100 | 100 | 100 | 102 | 81 | 71 | 27 | 21 | 11 |
| | 37°C | 100 | 107 | 112 | 109 | 112 | 102 | 100 | 96 | 39 |
| CATALASE CONTAINING SODIUM AZIDE | 4°C | 100 | 102 | 101 | 107 | 104 | 110 | 101 | 107 | 95 |
| | RT | 100 | 102 | 111 | 115 | 92 | 99 | 40 | 13 | 0.1 |
| | 37°C | 100 | 102 | 108 | 110 | 98 | 83 | 31 | 2 | 0.1 |

NOTE: ALL DATA ARE IN $\dfrac{\text{CHEMILUMINESCENCE SIGNAL OF A CONTROL SAMPLE CONTAINING AN ACCORDINGLY STORED CATALASE READY-TO-USE SOLUTION}}{\text{CHEMILUMINESCENCE SIGNAL OF THIS CONTROL SAMPLE CONTAINING A FRESH CATALASE READY-TO-USE SOLUTION}} \times 100\ (\%)$

RT = ROOM TEMPERATURE (18° TO 22°C)

FIG. 4

POSSIBLE SOURCES OF ERROR

| CAUSE | GLW | RLW | BK I | BK II | BKI/RLW | BKII/BKI | PRECISION | REMEDY |
|---|---|---|---|---|---|---|---|---|
| LIGHT GETS INTO MEASURING CHAMBER | ↑↑ | ↑↑ | | | | | | SEAL MEASURING CHAMBER LIGHT-TIGHT |
| INJECTOR DEFECTIVE | | | =GLW | =GLW | 1 | 1 | | REPAIR INJECTOR |
| CATALYST SOLUTION MISSING | | =GLW | =GLW | =GLW | 1 | 1 | | USE NEW CATALYST SOLUTION |
| PEROXIDE SOLUTION MISSING | | =GLW | =GLW | =GLW | 1 | 1 | | USE FRESH PEROXIDE SOLUTION |
| MEASURING VIAL CONTAMINATED | | ↑ | | | ↓ | | | CHANGE MEASURING VIAL |
| CATALYST SOLUTION CONTAMINATED | | ↑ | | | ↓ | | | USE NEW CATALYST SOLUTION |
| PEROXIDE SOLUTION CONTAMINATED | | ↑ | | | ↓ | | | USE FRESH PEROXIDE SOLUTION |
| CATALYST SOLUTION DECOMPOSED | | ↓ | ↑ | ↑ | <30 | <8.5 | | USE NEW CATALYST SOLUTION |
| PEROXIDE SOLUTION DECOMPOSED | | ↓ | ↑ | ↑ | <30 | | | USE FRESH PEROXIDE SOLUTION |
| PEROXIDE INCOMPLETELY DISSOLVED | | | | | | | ↕ | SHAKE PEROXIDE SOLUTION |
| PIPETTE DEFECTIVE - ERROR | | | | | | | ↕ | CHECK PIPETTES |
| INACCURATE INJECTOR OPERATION | | | | | | | ↕ | RINSE INJECTOR FOR CLEANING |
| BK I RECONSTITUTION ERROR | | | ↕ | | ↕ | ↕ | | RECONSTITUTE BK I AGAIN |
| BK II RECONSTITUTION ERROR | | | | ↕ | | ↕ | | RECONSTITUTE BK II AGAIN |
| BK I USED TWICE | | | | =BK I | | 1 | | REPEAT QUALITY CHECK |
| BK II USED TWICE | | | =BK II | | ↕ | 1 | | REPEAT QUALITY CHECK |
| BK I AND BK II INTERCHANGED | | | ↓ | ↓ | ↓ | <0.2 | | REPEAT QUALITY CHECK |

(↑↑ MUCH TOO HIGH; ↑ CLEARLY TOO HIGH; ↓ CLEARLY TOO LOW; ↕ CLEARLY DIFFERENT FROM EMPIRICAL VALUE)

LUMINESCENCE IMMUNO-TEST KITS, METHOD FOR STABILIZING SAME AND QUALITY CONTROL THEREOF

The present invention relates to luminescence immuno-test kits containing an antigen or antibody capable of showing luminescence and labelled with phthalic hydrazides, an antibody or antigen preferably bound to a carrier and an oxidizing reagent inducing the luminescence to occur, and methods for the stabilization of the reagents and quality control thereof.

BACKGROUND OF THE INVENTION

Luminescence immuno-tests are basically well suited for immunoassays as upon careful and competent handling they meet all requirements as to precision and limits of measurement in an optimum manner. However, so far this testing method has remained restricted to a few specialized laboratories, as the handling is relatively complicated and reliable results are obtained only with most careful and competent handling.

A further disadvantage of present luminescence immuno-tests is that the oxidizing reagents initiating luminescence are not storage-stable over long periods of time and, thus, always have to be freshly prepared. This in turn makes the required quality check very difficult and expensive.

Thus, it is a first object of the present invention to bring as many of the necessary reagents and components as possible into a stable form suitable for use in a simplified and reliable quality check.

In Applicant's German Patent Application No. P 34 39 742 there has been proposed a process for initiating light emission by oxidation of phthalic hydrazides in luminescence immuno-tests by the additon of pseudoperoxidase, aqueous sodium hydroxide and aqueous peroxide, wherein the pseudoperoxidase is added to the test batch prior to the measurement and the initiation of the light emission is effected by the addition of an alkaline peroxide solution which is from 0.3 to 10 hours old. Attempts to stabilize the microperoxidase in the dissolved state have failed, as this enzyme has a tendency to decompose, more particularly at elevated temperatures while being shipped or stored, and will lose its activity. Shroeder and Yeager (Analytical Chemistry, Vol. 50, No. 8, pages 1114–1120) investigated various oxidants in a comparative study, resulting in the finding that, hematin and microperoxidase are particulary well suitable as oxidants, subsequently microperoxidase was considered as the catalyst of first choice. However, unfortunately it is still necessary to freshly prepare the microperoxidase solution at least daily and to use it up on the same day. Applicant's investigations lead to the result that hemin and hematin do not give storage-stable solutions, either. Experiments with peroxidase, in comparison to microperoxidase, produced a significantly poorer signal yields, resulting in the finding that peroxidase is less than satisfactory for practical use.

SUMMARY OF THE INVENTION

It has surprisingly been found that the enzyme catalase, more specifically in a buffered form and in the presence of a bacteriostat, provides very stable solutions which also ensure good light yields to be obtained when used as a catalyst for initiating luminescence in immuno tests.

It was particularly surprising that not only antibiotics, but also sodium azide may be used as the bacteriostat. Since sodium azide has been known to be an enzyme poison, it was by no means foreseeable that this agent would be suitable for stabilizing a catalase solution for luminescence immuno-tests. As buffers for the catalase solution there are particularly well suitable (a) physiolofical saline (0.15 moles/l of NaCl), (b) 0.05 mole/l phosphate solution (pH 6), or both, if desired, with an addition of 10 micromoles/l of thymol.

Thus, the novel luminescence immuno-tests according to the invention are characterized in that the oxidizing reagent is a pre-fabricated solution of catalase, optionally stabilized by a bacteriostat, and the initiator is a pre-fabricated peroxide solution which is at least 20 minutes old.

DETAILED DESCRIPTION

Figure 1:
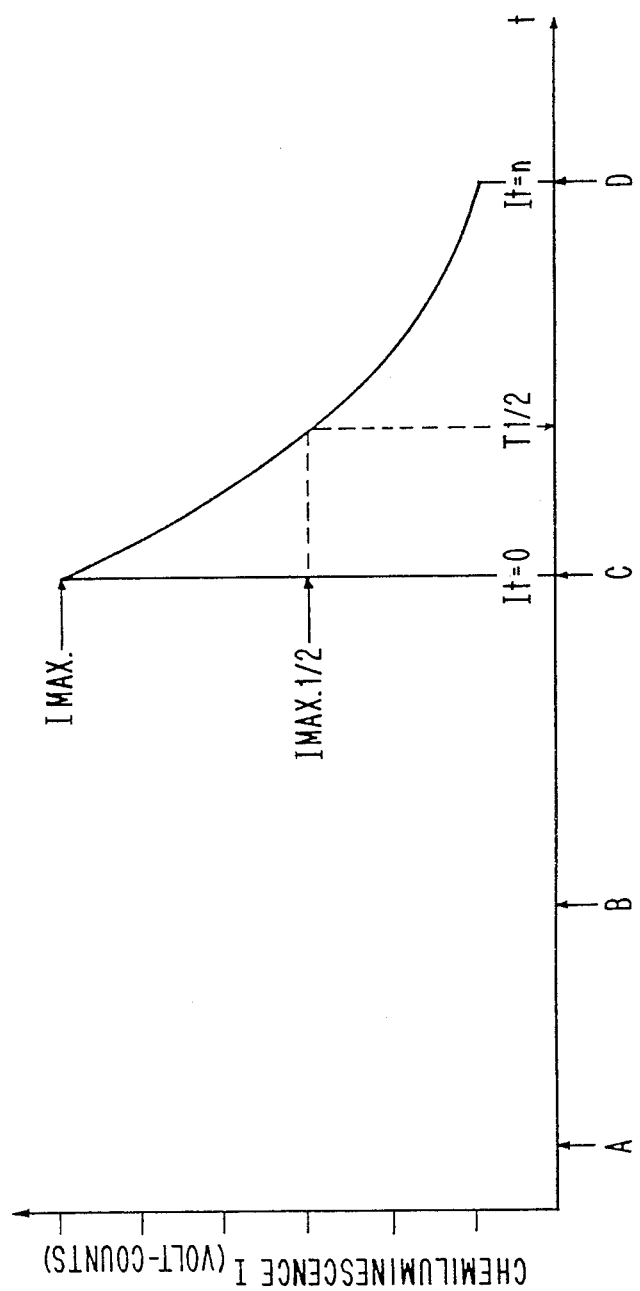

Complexed peroxides have proven to be useful, since they are storage stable in the solid state and in an alkaline solution, and when stored for at least 20 minutes, they are sufficiently stable for the duration of a day of measurements. Aging for 20 minutes is required since, during the first 20 minutes after mixing the peroxide and the alkali, a significant signal enhancement is observed in the luminescence immuno-test. This signal enhancement results in an essential improvement in sensitivity, particularly with respect to the lower limit of detection. However, this maturation process of the solution leads to a falsification of the measured values. Therefore, optimum results are obtained when the alkaline peroxide solutions are from 20 minutes to 10 hours old.

According to the invention it is now possible to stabilize luminescence immuno-tests consisting of an antigen or antibody capable of showing luminescence and labelled with phthalic hydrazides, an antibody or antigen preferably bound to a carrier and an oxidizing reagent inducing the luminescence to occur by adding the oxidizing reagent as a a pre-fabricated solution of catalase, optionally stabilized by a bacteriostat, and the initiator in a pre-fabricated peroxide solution which is at least 20 minutes old.

Particularly suitable peroxides for use in the present invention are, the solid complexed peroxides such as sodium peroxide, sodium percarbonate, sodium perborate, ammonium peroxodisulfate and commercialy available Perhydrit ® tablets in which hydrogen peroxide is bonded to urea.

As suitable phthalic hydrazides there may be mentioned 6-[-N-(4-aminobutyl-N-ethyl)isoluminol]hemisuccinamide (ABEI-H) as well as the hydrazides described in the U.S. Pat. Nos. 4,363,759, 4,334,069, 4,297,273, 4,225,485 and 4,331,808. Additionally, suitable phthalic hydrazides are those having a fused benzene ring such as the naphthyl hydrazides.

According to the invention it is now also possible to more simply and rapidly carry out the required quality control of the luminescence immuno-tests. This quality control should determine the unobjectionable conditions of the reagents inducing the luminescence and of the condition of the measuring equipment. It has been shown that the different concepts of the luminometers commercially available today may result in considerable deviation and unacceptable malfunctions. Depending on the type of measurement of the chemiluminescence signals, widely different units of measurement are obtained. Thus, some luminometers detect the chemiluminescence signals in the form of a photon flux (measured quantity=volt), while others do so by recording signle photon events (measured quantity=pulses or counts). Furthermore, it has been found that even with the use of several pieces of apparatus of the same instrument type and using identical reagents deviations from instrument to instrument of more than 20% were observed. This is obviously due to the difficulty of calibrating the photomultipliers employed in luminometers.

In the course of comparative investigations, not only of various reagents but also of different instruments, it has now surprisingly been observed that, on measuring defined chemiluminescent control samples, the measured values of which were differentiated from each other by a factor of between 2 and 100, and preferably of between 5 and 20, the ratio of the measured values of said control samples is constant within a relatively narrow margin irrespectively of the employed measuring instrument. It follows that the instruments and chemicals can be readily and reliably checked by means of only two control values I and II distinguished from each other by a defined factor (for example, of 10), if the following values are measured or calculated, respectively:
 (a) Instrument blank value (GLW)
 (b) Reagent blank value (RLW)
 (c) Control values I and II (KI and KII)
 (d) the ratio of KII/KI and
 (e) the ratio of KI/RLW.

In some cases it may be advisable to calculate the ratio of RLW/GLW in addition to the former data. It is possible to enter said value into a computer which in the case of a deviation from the set value will directly show possible sources of error.

Particularly surprising was the finding that, apart from determining the above-mentioned measured values and quotients which can be determined only prior to the assay, the quality control can be continued during the assay series as well, as in the actual measurements the signal half-value time $T_{\frac{1}{2}}$ is approximately constant.

Upon the measurement of this signal half-value time and comparison thereof to the initial value immediately after the calibration of the instrument, it is indicated whether all parameters are still in order and, therefore, reliable results can be expected. A gradual or sudden change in the signal half-value time indicates that either errors occurred in the instrument or regarding the reagents which can impair the reliability of the final result.

The instrument blank value (GLW) is determined by means of a measurement carried out without an addition of reagents. Here the value obtaned should be relatively small and conform to the empirical values reported by the manufacturer of the instrument. A deterioration caused by undesired extraneous light becomes manifest by extremely high pulse rates which often exceed the upper limit of detection of the instrument.

The reagent blank (RLW) value is determined by first injecting the catalase solution into a measuring cell, bringing the measuring cell into the measuring position, injecting the alkaline peroxide solution into the cell and then determining the luminescence. The respective measured values are generally higher than the GLW, however they must not exceed an upper limit determined from empirical values. If with a correct GLW the upper limit set for RLW is distinctly exceeded, this indicates that either one or both of the reagents inducing chemiluminescence are contaminated with a substance producing an unspecific chemiluminescence signal. Contaminated measuring cells or vials may also be causative factors. If, however, GLW is equal to RLW, this may be due to a use of reagents having become unusable or to a malfunctioning injection system.

The ratio of KII/KI should conform to the value to which the solutions I and II had been previously adjusted. The ratio of KI/RLW should be within the range between 20 to 70. In order to ensure a sufficient reliability, each measurement should be carried out at least in duplicate, or preferably in triplicate, and the average of these determinations should be evaluated. If the variation coefficient of these multiple analyses is in excess of 5%, the cause should be determined. With significant deviations of the quotients of KII/KI and KI/RLW, the degree and kind of the deviations suggest certain errors to have occurred so that determinations may be made accordingly.

Due to the fact that with a proper instrument and with unobjectionable reagents the signal half-value-time $T_{\frac{1}{2}}$ is approximately constant, the measurment of this parameter enables any individual measured value to be checked regularly. It has further been shown that the measurements and calculations, respectively, of the above measured data and quotients, and, specifically, of the signal half-value-time, are applicable not only to the luminescence immuno-tests according to the invention, but in the same manner also to other tests in which acridine-labelled antigens or antibodies are used as the luminescent system. As the acridine derivatives there are particularly suitable the substances described in the European Published Patent Application EP No.-05 0 082 636.

Thus, a further object of the invention is to provide a method for the quality control of luminescence immuno-tests consisting of an antigen or antibody capable of showing luminescence and labelled with phthalic hydrazides or acridine groups, an antibody or antigen preferably bound to a carrier and an oxidizing reagent inducing the luminescence, which method is characterized in that the oxidizing reagent, if required, is a pre-fabricated solution of catalase, optionally stabilized by a bacteriostat, and the initiator is a pre-fabricated peroxide solution which is at least 20 minutes old, and that the following values are measured or calculated, respectively:
 (a) Instrument blank value (GLW)
 (b) Reagent blank value (RLW)
 (c) Control values I and II (KI and KII)
 (d) the ratio of KII/KI and
 (e) the ratio of KI/RLW.

It is preferred that the measured or calculated values of (a) through (e) are entered into a computer which, in the case of deviations determined upon comparison with respective pre-set values, displays possible sources of error. Preferably, the signal half-value-time $T_{\frac{1}{2}}$ is measured in addition to the former and compared to a pre-set value which permits a permanent quality control to be accomplished.

In some special cases and when certain types of instruments are employed, it also may be useful to calculate the ratio of RLW/GLW in order to draw attention to some possible sources of error in the case of a deviation of said ratio from a pre-set value.

The luminescence immuno-test kits according to the invention, the method for stabilizing same and the method for the quality control thereof are further illustrated in the following non-limiting examples.

EXAMPLE 1

Preparation of a ready-to-use and storage stable catalase solution:

$4-20\times10^6$ units of catalase obtained from bovine liver, molecular weight of about 240,000, are dissolved in 1 liter of a 0.15 moles/l NaCl solution containing 0.1% (w/v) of sodium azide. One unit of catalase, according to the definition, is the amount reacting 1 micromole of hydrogen peroxide per minute at a pH of 7.0 and a temperature of 25° C. The final concentration in units of catalase per liter to be selected will depend on the quality of the reagent additionally required or used, respectively, for initiating the chemiluminescence signal of phthalic hydrazides or derivatives thereof and may accordingly be adjusted or optimized.

The solution described hereinbefore is stable at 4° C. for 6 months and at room temperature for 2 months. Even at 37° C. it still has a storage stability of 35 days.

The same catalase solution, however, without the addition of sodium azide, is even somewhat more stable in storage, particularly at elevated temperature. However it is susceptible to bacterial infection. The measured values for the long-time stability of catalase solutions according to the invention are shown in the attached FIG. 2.

From the results it is readily apparent that the catalase solution may be readily shipped from the producer to the consumer even during the summer months without concern that the solution will become unusable. Due to the addition of sodium azide, no bacterial growth has been observed even after six months. The enzyme activity is deteriorated by this additive only to a negligible degree.

The measured values set forth in FIG. 2 were obtained as follows: 100 μl of a control sample (phthalic hydrazide derivative-labelled protein) capable of producing a defined chemiluminescence signal in a Berthold Luminometer LB 9500 were mixed with 300 μl of a ready-to-use catalase solution stored under the conditions as set forth. The sample was placed in the measuring position and the chemiluminscence reaction was initiated by the injection of 300 μl of alkaline peroxide solution. The signals obtained were compared to those obtained with a freshly prepared catalase solution and indicated in percent.

EXAMPLE 2

Preparation of alkaline peroxide solutions:

Solution A 100 mg of sodium percarbonate ($2\, Na_2CO_3 \times 3\, H_2O_2$) are dissolved in 100 ml of 0.2N sodium hydroxide solution. This solution is allowed to stand at room temperature for 30 minutes. For initiating the chemiluminescence signals of phthalic hydrazide derivatives and acridinium derivatives, 300 μl of this solution are injected into suitable measuring cells or vials placed in the measuring position and containing the sample to be assayed. The solution is stable at room temperature (18° C. to 22° C.) for at least one day of measuring and at refrigerator temperature (4° C.) for about 7 days. 100 mg of sodium percarbonate contain the same amount of active oxygen as about 80 mg of a 35% hydrogen peroxide solution.

Solution B 200 mg of sodium perborate ($NaBO_2 \times H_2O_2 \times 3\, H_2O$) are dissolved in 100 ml of 0.2 N sodium hydroxide solution. Use is made as for solution A. Solution B is stable at room temperature (18° C. to 22° C.) for at least one day of measuring and at refrigerator temperature (4° C.) for at least 10 days. 100 mg of sodium perborate contain the same amount of active oxygen as about 61 mg of a 35% hydrogrn peroxide solution.

Solution C

One tablet (1 g) of Perhydrit ® is dissolved in 100 ml of 1N sodium hydroxide solution. Use is made as for solution A. Solution C is stable at room temperature (18° C. to 22° C.) for at least one day of measuring and at refrigerator temperature (4° C.) for at least 10 days. 1 tablets (=1 g) of Perhydrit ® contains the same amount of active oxygen as about 1 g of a 35% hydrogen peroxide solution.

EXAMPLE 3

Luminescence immuno-test kit:

For the luminescence immuno-tests two separate packages are prepared as follows:

Immuno kit (sufficient for 100 determinations)

In separate flasks, amounts sufficient for 100 determinations of carrier-bound antibody or antigen and antibodies or antigens labelled with a phthalic hydrazide derivatives are packed, as is a standard dilution series designed for the calibration and containing defined concentrations of the antigen and antibody, respectively. For immunotests, e.g. according to a sandwich method, a corresponding antigen- or species-specific antibody is also provided. These immuno kits are made up so as to fit the intended use, but, they are altogether usable in combination with the following reagent kit.

Reagent kit (for 1,000 to 5,000 determinations)

In the reagent kit there are combined the azide-stabilized catalase solution, a solid complexed peroxide and 1N sodium hydroxide solution as well as control solutions I and II containing the luminescent derivative.

For practical application the peroxide is dissolved in the sodium hydroxide solution. This solution is ready for use after 20 minutes of aging and stable at least during the whole day of measuring.

EXAMPLE 4

Quality control:

For a number of different luminometers the instrument blank values (GLW), the reagent blank values (RLW), and the control values I and II (KI and KII) were measured, and the quotients of KII/KI and KI/RLW were calculated. The initiation of the chemiluminescence signals was caused by the above-described catalase solution and the alkaline peroxide solution. Each value was measured in triplicate, and the average was used for the valuation. All of the variation coefficients were below 5%.

The results of the measurements are shown in the following Table.

| Luminometer Type of Instrument | Measuring Period | RLW | K I | K II | K II/K I | K I/RLW |
|---|---|---|---|---|---|---|
| LKB 1251 | 20 sec. | 10 (mV) | 349 | 3079 | 8.82 | 34.9 |
| Berthold LB 950 | 10 sec. | 12 (pulses × $10^{-3}$) | 540 | 5350 | 9.9 | 45 |
| Berthold LB 9500 Instrument No. 1 | 10 sec. | 664 pulses | 22516 | 214070 | 9.51 | 33.9 |
| Berthold LB 9500 Instrument No. 2 | 10 sec. | 899 pulses | 31352 | 298094 | 9.5 | 34.9 |
| Berthold LB 9500 Instrument No. 3 | 10 sec. | 1314 pulses | 39784 | 406095 | 10.2 | 30.2 |
| Berthold LB 9500 Instrument No. 4 | 10 sec. | 620 pulses | 21376 | 218080 | 10.2 | 34.5 |

In order to check the effects of typical errors in the reagents, said errors were intentionally caused to occur. For this purpose, using a Luminometer Berthold LB 9500 and reagents according to the invention as described above and reagents intentionally modified so as to make them defective, the following values were measured and calculated, respectively, for the condition and error condition set forth below:

| (Error) Condition | RLW pulses | K I pulses | K II pulses | K II/K I | K I/RLW |
|---|---|---|---|---|---|
| Instrument blank value (GLW) average = 40 pulses | | | | | |
| Intact reference | 640 | 36270 | 367116 | 10.1 | 56.67 |
| Use of H$_2$O instead of sodium hydroxide solution | 70 | 61 | 64 | 1.05 | 0.86 |
| Peroxide addition forgotten | 62 | 61 | 66 | 1.08 | 1.06 |
| Catalyst addition forgotten | 81 | 96 | 106 | 1.19 | 1.31 |
| Catalyst diluted by 10 times | 83 | 7117 | 66818 | 9.39 | 85.75 |
| Catalyst diluted by 100 times | 68 | 980 | 6739 | 6.88 | 14.41 |
| 50% of alkaline peroxide solution decomposed | 655 | 27300 | 264400 | 9.68 | 41.68 |
| 95% of alkaline peroxide solution decomposed | 430 | 6380 | 58162 | 9.12 | 14.84 |

Following is a typical example of results as printed by a computer during a quality control check on the measuring instruments, the catalase, and the alkaline peroxide ready-to-use solutions prepared according to this invention:

```
                              * * * * * * * * *
                              (Quality Control)
                              (Date)
                              * * * * * * * * *
                              GLW1 37
                              GLW2 41
                              GLW 39
                              RLW1 673
                              RLW2 660
                              RLW3 657
                              RLW4 668
                              RLW 664.5
                              (Control ..)
                              Control I 1 23209
                              Control I 2 22381
                              Control I 3 21995
                              Control II 1 220195
                              Control II 2 210722
                              Control II 3 211293
                              Control I 22516
                              Control II 214070
                              (Precision ..)
                              Precision I 2.8%
                              Precision II 2.5%
                              K II/K I 9.51
                              K I/RLW 33.9
Measuring System              Measuring System and Apparatus
Instrument ok                 in Order
```

Figure 3:
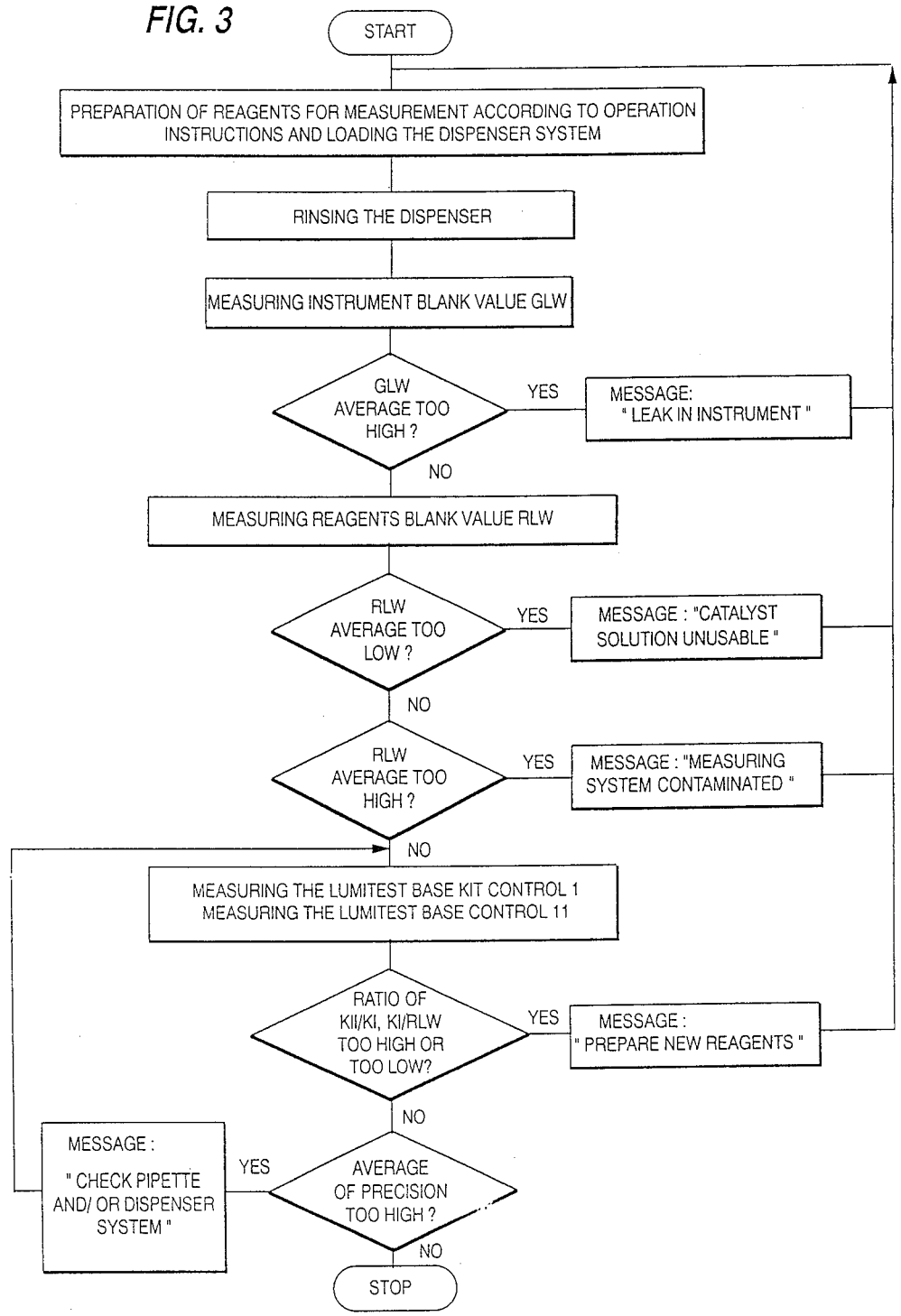

A typical example of an operational chart for running a quality check program for examining the measuring instrument and and of the catalase and alkaline peroxide ready-to-use solutions prepared according to the invention is shown in the attached FIG. 3.

The course during the lapse of time of a chemiluminescence measurement using the reagents prepared according to the invention is shown in the attached FIG. 1:

After the addition of the catalyst (catalase ready-to-use solution) to the sample to be investigated at the time instant A (which is not required, for example, if acridine derivatives are employed), the measuring vial containing the sample is put into the luminometer (time instant B). In the measurement position, by means of a suitable injection system, the ready-to-use alkaline peroxide solution is injected (time instant C) and the chemiluminescence measurement is started. As the measured character there is used the integral of the light intensity (area under the curve AUC of the light intensity over the time between the time $t=0$ (time instant C) and the time $t=n$ (with n representing the period of measurement) at the time instant D. The signal half-value time $T_{\frac{1}{2}}$ is apparent from the point of time at which half of the value of the maximum intensity $I_{max}$ has been reached. When well adjusted instruments and unobjectionable reagents are employed, this value is approximately constant in the course of the whole day and, thus, provides an indication that the system continues to be fully useful.

The extensive measurements carried out with the use of the system of the invention showed that the stability of the catalase solution can be further improved by an addition of ethanol and EDTA. These additives are capable of preventing the observed slow shift from higher to lower values in the course of some hours. Ethanol acts as a very slowly reacting substrate of catalase, but reacts significantly more slowly than peroxide. In the absence of peroxide, some ethanol is slowly oxidized by catalase and oxygen of the air, but the chemiluminescent properties of the phthalic hydrazide are not affected. EDTA acts as a complexing agent for divalent metal ions which may also slowly initiate the chemiluminescence of the phthalic hydrazides.

Therefore, an optimal catalase solution has the composition as follows:

$4-20\times 10^6$ units of catalase from bovine liver, molecular weight of about 240,000, dissolved in 1 liter of a 0.15 moles/l NaCl solution containing 0.1% (w/v) of sodium azide, ethanol (1 to 10%, and preferably 3%) and EDTA sodium salt (ethylenediamine tetraacetate) (0.1 to 5 g/l, and preferably 1 g/l).

The table of FIG. 4 shows possible errors, their causes and remedies.

What is claimed is:

1. Luminescence immuno-test kit consisting essentially of an antigen or antibody labeled with a phthalic hydrazide capable of showing luminescence, an antibody or antigen and an oxidizing agent inducing the luminescence to occur, characterized in that the oxidizing agent is a pre-fabricated solution of catalase and that an initiator is a pre-fabricated peroxide solution which is at least 20 minutes old.

2. Kit according to claim 1 wherein the solution of catalase is stabilized by a bacteriostatic agent.

3. Kit according to claim 2, characterized in that sodium azide is used as bacteriostatic agent.

4. Kit according to claim 1, characterized in that a complexed peroxide is used as the peroxide.

5. Kit according to claim 2, wherein a complexed peroxide is used as peroxide.

6. A kit according to claim 1 wherein said catalase solution additionally contains 1 to 10% ethanol and 0.1 to 5 g/l EDTA.

7. A kit according to claim 2 wherein said catalase solution additionally contains 1 to 10% ethanol and 0.1 to 5 g/l EDTA.

8. Method for providing stablized luminescence immuno-test kits consisting essentially of an antigen or antibody labeled with a phthalic hydrazide capable of showing luminescence, an antibody or antigen and an oxidizing reagent inducing said luminescence to occur wherein stabilization is effected by adding said oxidizing reagent in the form of a pre-fabricated solution of catalase, and an initiator is added in the form of a pre-fabricated peroxide solution which is at least 20 minutes old.

9. Method of claim 8 wherein the solution of catalase is stabilized by a bacteriostatic agent.

10. Method according to claim 9, characterized in that sodium azide is used as bacteriostatic agent.

11. Method according to claim 8, characterized in that a complexed peroxide is used as the peroxide.

12. Method according to claim 10, characterized in that a complexed peroxide is used as the peroxide.

13. The method according to claim 8 wherein said catalase solution additionally contains 1 to 10% ethanol and 0.1 to 5 g/l EDTA.

14. The method according to claim 10 wherein said catalase solution additionally contains 1 to 10% ethanol and 0.1 to 5 g/l EDTA.

* * * * *